United States Patent
Hecht et al.

(10) Patent No.: US 12,110,313 B2
(45) Date of Patent: Oct. 8, 2024

(54) ENGINEERED BACTERIAL RIBOSOME COMPOSITIONS AND METHODS

(71) Applicants: Sidney Hecht, Phoenix, AZ (US); Larisa Dedkova, Scottsdale, AZ (US); Shengxi Chen, Chandler, AZ (US); Xiaoguang Bai, Scottsdale, AZ (US)

(72) Inventors: Sidney Hecht, Phoenix, AZ (US); Larisa Dedkova, Scottsdale, AZ (US); Shengxi Chen, Chandler, AZ (US); Xiaoguang Bai, Scottsdale, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 142 days.

(21) Appl. No.: 16/804,691

(22) Filed: Feb. 28, 2020

(65) Prior Publication Data

US 2020/0299333 A1    Sep. 24, 2020

Related U.S. Application Data

(60) Provisional application No. 62/811,638, filed on Feb. 28, 2019.

(51) Int. Cl.
  *C07K 14/00* (2006.01)
  *C07H 19/16* (2006.01)
  *C07K 14/565* (2006.01)

(52) U.S. Cl.
  CPC ........... *C07K 14/001* (2013.01); *C07H 19/16* (2013.01); *C07K 14/565* (2013.01)

(58) Field of Classification Search
  CPC ....... C07K 14/001; C07K 14/565; C07H 9/16
  See application file for complete search history.

(56) References Cited

U.S. PATENT DOCUMENTS

| | | |
|---|---|---|
| 8,952,025 B2 | 2/2015 | Hecht |
| 9,102,626 B2 | 8/2015 | Hecht |
| 9,334,250 B2 | 5/2016 | Chowdhury et al. |
| 9,388,163 B2 | 7/2016 | Hecht |
| 10,472,340 B2 | 11/2019 | Jecht |
| 10,604,501 B2 | 3/2020 | Chevalier et al. |
| 10,745,366 B2 | 8/2020 | Hecht |
| 10,745,705 B2 | 8/2020 | Hecht |
| 2011/0293530 A1 | 12/2011 | Hecht |
| 2013/0266518 A1 | 10/2013 | Hecht |
| 2018/0002709 A1* | 1/2018 | Hecht ................ C07D 277/593 |
| 2020/0115355 A1 | 4/2020 | Hecht |
| 2020/0247775 A1 | 8/2020 | Chevalier et al. |
| 2020/0370057 A1 | 11/2020 | Hecht |
| 2020/0407333 A1 | 12/2020 | Hecht |

FOREIGN PATENT DOCUMENTS

WO    2010006153 A2    1/2010

OTHER PUBLICATIONS

Bowie et al (Science, 1990, 257:1306-1310).*
Burgess et al (J. of Cell Bio. 111:2129-2138, 1990).*
Lazar et al. (Molecular and Cellular Biology, 1988, 8:1247-1252).*
Bork (Genome Research, 2000, 10:398-400).*
Zarschler, K., et al. (2010). Protein tyrosine O-glycosylation—a rather unexplored prokaryotic glycosylation system. Glycobiology, 20(6), 787-798.
Zhang, Z. Y. (2002). Protein tyrosine phosphatases: structure and function, substrate specificity, and inhibitor development. Annual review of pharmacology and toxicology, 42(1), 209-234.
Zhang, Z., et al. (2003). The role of C-terminal tyrosine phosphorylation in the regulation of SHP-1 explored via expressed protein ligation. Journal of Biological Chemistry, 278(7), 4668-4674.
Zheng, W., et al. (2003). Cellular stabilization of the melatonin rhythm enzyme induced by nonhydrolyzable phosphonate incorporation. Nature Structural & Molecular Biology, 10(12), 1054-1057.
U.S. Appl. No. 16/327,287, filed Feb. 21, 2019, Hecht et al.
Acevedo-Morantes, C. Y., et al. (2012). Cytotoxicity and reactive oxygen species generated by ferrocenium and ferrocene on MCF7 and MCF10A cell lines. J Cancer Sci Ther, 4(9), 271-275.
Arslan, T., et al. (1997). Structurally modified firefly luciferase. Effects of amino acid substitution at position 286. Journal of the American Chemical Society, 119(45), 10877-10887.
Baeuerle, P. A., et al. (1988). I kappa B: a specific inhibitor of the NF-kappa B transcription factor. Science, 242(4878), 540-546.
Batjargal, S., et al. (2012). Native chemical ligation of thioamide-containing peptides: development and application to the synthesis of labeled a-synuclein for misfolding studies. Journal of the American Chemical Society, 134(22), 9172-9182.
Bäumer, N., et al. (2007). Expression of protein histidine phosphatase in *Escherichia coli*, purification, and determination of enzyme activity. In Protein Phosphatase Protocols (pp. 247-260).
Beese, L. S., et al. (1993). Structure of DNA polymerase I Klenow fragment bound to duplex DNA. Science, 260(5106), 352-355.
Beg, A. A., et al. (1992). I kappa B interacts with the nuclear localization sequences of the subunits of NF-kappa B: a mechanism for cytoplasmic retention. Genes & development, 6(10), 1899-1913.
Bernardes, G. J., et al. (2008). Facile conversion of cysteine and alkyl cysteines to dehydroalanine on protein surfaces: versatile and switchable access to functionalized proteins. Journal of the American Chemical Society, 130(15), 5052-5053.
Brockman, J. A., et al. (1995). Coupling of a signal response domain in I kappa B alpha to multiple pathways for NF-kappa B activation. Molecular and cellular biology, 15(5), 2809-2818.
Brown, K., et al. (1995). Control of I kappa B-alpha proteolysis by site-specific, signal-induced phosphorylation. Science, 267(5203), 1485-1488.
Burda, P., et al. (1999). The dolichol pathway of N-linked glycosylation. Biochimica et Biophysica Acta (BBA)-General Subjects, 1426(2), 239-257.

(Continued)

*Primary Examiner* — Robert A Zeman
(74) *Attorney, Agent, or Firm* — Quarles & Brady, LLP

(57) ABSTRACT

Compositions and methods relating to bacterial ribosomes selected to increase the incorporation of at least one glycosylated amino acid into a protein versus a wild-type bacterial ribosome. Selection embodiments include growing bacteria in the presence of a puromycin derivative, wherein a surviving clone has a ribosome that incorporates at least one glycosylated amino acid into a protein.

11 Claims, 6 Drawing Sheets

Specification includes a Sequence Listing.

(56) References Cited

OTHER PUBLICATIONS

Camps, M., et al. (2000). Dual specificity phosphatases: a gene family for control of MAP kinase function. The FASEB Journal, 14(1), 6-16.

Chowdhury, S. R., et al. (2016). Synthesis and evaluation of a library of fluorescent dipeptidomimetic analogues as substrates for modified bacterial ribosomes. Biochemistry, 55(17), 2427-2440.

Civas, A., et al. (1988). Purification and carbohydrate structure of natural murine interferon-β. European journal of biochemistry, 173(2), 311-316.

Cole, P. A., et al. (2003). Chemical approaches to reversible protein phosphorylation. Accounts of chemical research, 36(6), 444-452.

Dean, N. (1999). Asparagine-linked glycosylation in the yeast Golgi. Biochimica et Biophysica Acta (BBA)—General Subjects, 1426(2), 309-322.

Dedkova, L. M., et al. "β-Puromycin selection of modified ribosomes for in vitro incorporation of β-amino acids." Biochemistry 51.1 (2012): 401-415.

Deiters, A., et al. (2003). Adding amino acids with novel reactivity to the genetic code of Saccharomyces cerevisiae. Journal of the American Chemical Society, 125(39), 11782-11783.

Dell, A., et al. (2001). Glycoprotein structure determination by mass spectrometry. Science, 291(5512), 2351-2356.

Doucey, M. A., et al. (1999). Recombinant human interleukin-12 is the second example of a C-mannosylated protein. Glycobiology, 9(5), 435-441.

Doucey, M. A., et al. (1998). Protein C-mannosylation is enzyme-catalysed and uses dolichyl-phosphate-mannose as a precursor. Molecular biology of the cell, 9(2), 291-300.

Dwek, R. A. (1996). Glycobiology: toward understanding the function of sugars. Chemical reviews, 96(2), 683-720.

Fahmi, N. E., et al. (2001). Studies toward the site specific incorporation of sugars into proteins: Synthesis of glycosylated aminoacyl-tRNAs. Carbohydrate research, 330(2), 149-164.

Fahmi, N. E., et al. "Site-specific incorporation of glycosylated serine and tyrosine derivatives into proteins." Journal of the American Chemical Society 129.12 (2007): 3586-3597.

Gadsby, D. C., et al. (1999). Control of CFTR channel gating by phosphorylation and nucleotide hydrolysis. Physiological reviews, 79(1), S77-S107.

Garcia-Garcia, T., et al. (2016). Role of protein phosphorylation in the regulation of cell cycle and DNA-related processes in bacteria. Frontiers in microbiology, 7, 184.

Gemmill, T. R., et al. (1999). Overview of N-and O-linked oligosaccharide structures found in various yeast species. Biochimica et Biophysica Acta (BBA)—General Subjects, 1426(2), 227-237.

Ghosh, S., et al. (1990). Activation in vitro of NF-kB" by phosphorylation of its inhibitor IkB". Nature, 344(6267), 678-682.

Goldberg, J. M., et al. (2010). Thioamides as fluorescence quenching probes: minimalist chromophores to monitor protein dynamics. Journal of the American Chemical Society, 132(42), 14718-14720.

Goldberg, J. M., et al. (2013). Thioamide quenching of fluorescent probes through photoinduced electron transfer: mechanistic studies and applications. Journal of the American Chemical Society, 135(49), 18651-18658.

Goldberg, J. M., et al. (2012). Minimalist probes for studying protein dynamics: thioamide quenching of selectively excitable fluorescent amino acids. Journal of the American Chemical Society, 134(14), 6088-6091.

Grimsrud, P. A., et al. (2010). Phosphoproteomics for the masses. ACS chemical biology, 5(1), 105-119.

Hahn, M. E., et al. (2004). Photocontrol of Smad2, a Multiphosphorylated Cell-Signaling Protein, Through Caging of Activating Phosphoserines. Angewandte Chemie (International ed. in English), 43(43), 5800-5803.

Han, J. D. J., et al. (2004). Evidence for dynamically organized modularity in the yeast protein-protein interaction network. Nature, 430(6995), 88-93.

Hanger, D. P., et al. (1998). New phosphorylation sites identified in hyperphosphorylated tau (paired helical filament-tau) from Alzheimer's disease brain using nanoelectrospray mass spectrometry. Journal of neurochemistry, 71(6), 2465-2476.

Hartmann, S., et al. (2000). Properdin, the Positive Regulator of Complement, Is HighlyC-Mannosylated. Journal of Biological Chemistry, 275(37), 28569-28574.

Heckler, T. G., et al. (1984). Preparation of 2,('3)-O-Acyl-pCpA derivatives as substrates for T4 RNA ligase-mediated "chemical aminoacylation". Tetrahedron, 40(1), 87-94.

Heinemann, I. U., et al. (2012). Enhanced phosphoserine insertion during Escherichia coli protein synthesis via partial UAG codon reassignment and release factor 1 deletion. FEBS letters, 586(20), 3716-3722.

Hunter, T. (2000). Signaling—2000 and beyond. Cell, 100(1), 113-127.

Imbert, V., et al. (1996). Tyrosine phosphorylation of IkB-a activates NF-kB without proteolytic degradation of IkB-a. Cell, 86(5), 787-798.

Jung, S. T., et al. (2011). Bypassing glycosylation: engineering aglycosylated full-length IgG antibodies for human therapy. Current opinion in biotechnology, 22(6), 858-867.

Kajihara, D., et al. (2005). Synthesis and sequence optimization of GFP mutants containing aromatic non-natural amino acids at the Tyr66 position. Protein Engineering Design and Selection, 18(6), 273-278.

Kang, H. J., et al. (2014). The transcriptional complex between the BCL2 i-motif and hnRNP LL is a molecular switch for control of gene expression that can be modulated by small molecules. Journal of the American Chemical Society, 136(11), 4172-4185.

Kendrick, S., et al. (2014). The dynamic character of the BCL2 promoter i-motif provides a mechanism for modulation of gene expression by compounds that bind selectively to the alternative DNA hairpin structure. Journal of the American Chemical Society, 136(11), 4161-4171.

Kornfeld, R., et al. (1985). Assembly of asparagine-linked oligosaccharides. Annual review of biochemistry, 54(1), 631-664.

Krieg, J., et al. (1997). C-Mannosylation of human RNase 2 is an intracellular process performed by a variety of cultured cells. Journal of Biological Chemistry, 272(42), 26687-26692.

Lahiry, P., et al. (2010). Kinase mutations in human disease: interpreting genotype-phenotype relationships. Nature Reviews Genetics, 11(1), 60-74.

Latham, J. A., et al. (2007). Cross-regulation of histone modifications. Nature structural & molecular biology, 14(11), 1017-1024.

Lechner, J., et al. (1989). Structure and biosynthesis of prokaryotic glycoproteins. Annual review of biochemistry, 58(1), 173-194.

Liu, C. C., et al. (2006). Recombinant expression of selectively sulfated proteins in Escherichia coli. Nature biotechnology, 24(11), 1436-1440.

Liu, C. C., et al. (2010). Adding new chemistries to the genetic code. Annual review of biochemistry, 79, 413-444.

Liu, W. R., et al. (2011). Synthesis of proteins with defined posttranslational modifications using the genetic noncanonical amino acid incorporation approach. Molecular BioSystems, 7(1), 38-47.

Loffler, A., et al. (1996). Spectroscopic and protein chemical analyses demonstrate the presence of C-mannosylated tryptophan in intact human RNase 2 and its isoforms. Biochemistry, 35(37), 12005-12014.

Lu, W., et al. (2001). Site-specific incorporation of a phosphotyrosine mimetic reveals a role for tyrosine phosphorylation of SHP-2 in cell signaling. Molecular cell, 8(4), 759-769.

Maini, R., et al. (2015). Protein synthesis with ribosomes selected for the incorporation of β-amino acids. Biochemistry, 54(23), 3694-3706.

Maini, R., et al. (2015). Ribosome-mediated incorporation of dipeptides and dipeptide analogues into proteins in vitro. Journal of the American Chemical Society, 137(35), 11206-11209.

Maini, R., et al. (2013). Incorporation of β-amino acids into dihydrofolate reductase by ribosomes having modifications in the peptidyltransferase center. Bioorganic & medicinal chemistry, 21(5), 1088-1096.

(56) References Cited

OTHER PUBLICATIONS

Mamaev, S. V., et al. (1996). Firefly luciferase: alteration of the color of emitted light resulting from substitutions at position 286. Journal of the American Chemical Society, 118(30), 7243-7244.

Manning, G., et al. (2002). The protein kinase complement of the human genome. Science, 298(5600), 1912-1934.

Maverakis, E., et al. (2015). Glycans in the immune system and The Altered Glycan Theory of Autoimmunity: a critical review. Journal of autoimmunity, 57, 1-13.

Melo Czekster, C.,et al. (2016). In vivo biosynthesis of a β-amino acid-containing protein. Journal of the American Chemical Society, 138(16), 5194-5197.

Mescher, M. F., et al. (1976). Structural (shape-maintaining) role of the cell surface glycoprotein of Halobacterium salinarium. Proceedings of the National Academy of Sciences, 73(8), 2687-2691.

Messner, P. (1997). Bacterial glycoproteins. Glycoconjugate journal, 14(1), 3-11.

Mijakovic, I., et al. (2006). Bacterial single-stranded DNA-binding proteins are phosphorylated on tyrosine. Nucleic acids research, 34(5), 1588-1596.

Mosavi, L. K., et al. (2004). The ankyrin repeat as molecular architecture for protein recognition. Protein science, 13(6), 1435-1448.

Mumby, M. C., et al. (1993). Protein serine/threonine phosphatases: structure, regulation, and functions in cell growth. Physiological reviews, 73(4), 673-699.

Nathans, D., et al. (1963). Structural requirements for puromycin inhibition of protein synthesis. Nature, 197(4872), 1076-1077.

Noren, C. J., et al. (1990). In vitro suppression of an amber mutation by a chemically aminoacylated transfer RNA prepared by runoff transcription. Nucleic acids research, 18(1), 83-88.

Olsen, J. V., et al. (2006). Global, in vivo, and site-specific phosphorylation dynamics in signaling networks. Cell, 127(3), 635-648.

Park, H. S., et al. (2011). Expanding the genetic code of *Escherichia coli* with phosphoserine. Science, 333(6046), 1151-1154.

Pawson, T., et al. (2000). Protein-protein interactions define specificity in signal transduction. Genes & development, 14(9), 1027-1047.

Petranovic, D., et al. (2007). Bacillus subtilis strain deficient for the protein-tyrosine kinase PtkA exhibits impaired DNA replication. Molecular microbiology, 63(6), 1797-1805.

Rigden, D. J. (2008). The histidine phosphatase superfamily: structure and function. Biochemical Journal, 409(2), 333-348.

Robertson, S. A., et al. (1989). The use of 5'-phospho-2 deoxyribocytidylylriboadenosine as a facile route to chemical aminoacylation of tRNA. Nucleic acids research, 17(23), 9649-9660.

Rodriguez, M. S., et al. (1995). Inducible degradation of I kappa B alpha in vitro and in vivo requires the acidic C-terminal domain of the protein. Molecular and Cellular Biology, 15(5), 2413-2419.

Rothman, D. M., et al. (2005). Caged phosphoproteins. Journal of the American Chemical Society, 127(3), 846-847.

Rowan, F. C., et al. (2013). Insights into Aurora—A kinase activation using unnatural amino acids incorporated by chemical modification. ACS chemical biology, 8(10), 2184-2191.

Roy, B., et al. "Interaction of individual structural domains of hnRNP LL with the BCL2 promoter i-motif DNA." Journal of the American Chemical Society 138.34 (2016): 10950-10962.

Ruddon, R. W., et al. (1997). Assisted protein folding. Journal of Biological Chemistry, 272(6), 3125-3128.

Saxl, R. L., et al. (2001). Synthesis and biochemical characterization of a phosphorylated analogue of the response regulator CheB. Biochemistry, 40(43), 12896-12903.

Scherer, D. C., et al. (1995). Signal-induced degradation of I kappa B alpha requires site-specific ubiquitination. Proceedings of the National Academy of Sciences, 92(24), 11259-11263.

Serwa, R., et al. (2009). Chemoselective Staudinger-phosphite reaction of azides for the phosphorylation of proteins. Angewandte Chemie International Edition, 48(44), 8234-8239.

Shental-Bechor, D., et al. (2009). Folding of glycoproteins: toward understanding the biophysics of the glycosylation code. Current opinion in structural biology, 19(5), 524-533.

Silversmith, R. E., et al. (1998). Synthesis and characterization of a stable analog of the phosphorylated form of the chemotaxis protein CheY. Protein engineering, 11(3), 205-212.

Sommereyns, C., et al. (2006). N-glycosylation of murine IFN-β in a putative receptor-binding region. Journal of Interferon & cytokine research, 26(6), 406-413.

Spiro, R. G. (2002). Protein glycosylation: nature, distribution, enzymatic formation, and disease implications of glycopeptide bonds. Glycobiology, 12(4), 43R-56R.

Tarrant, M. K., et al. The chemical biology of protein phosphorylation. Annual review of biochemistry, 78, 797-825. 2009.

Taylor, S. S., et al. (2011). Protein kinases: evolution of dynamic regulatory proteins. Trends in biochemical sciences, 36(2), 65-77.

Traenckner, E. M., et al. (1995). Phosphorylation of human I kappa B-alpha on serines 32 and 36 controls I kappa B-alpha proteolysis and NF-kappa B activation in response to diverse stimuli. The EMBO journal, 14(12), 2876-2883.

Trombetta, E. S. (2003). The contribution of N-glycans and their processing in the endoplasmic reticulum to glycoprotein biosynthesis. Glycobiology, 13(9), 77R-91R.

Verma, I. M. (1994). Tumor necrosis factor a-induced phosphorylation of IKBa is a signal for its degradation but not dissociation from NF-KB. Proc. Natl. Acad. Sci. USA, 91, 12740-12744.

Verma, I. M., et al. (1995). Rel/NF-kappa B/I kappa B family: intimate tales of association and dissociation. Genes & development, 9(22), 2723-2735.

Vogel, E. M., et al. (2007). Semisynthesis of unnatural amino acid mutants of paxillin: protein probes for cell migration studies. Protein science, 16(3), 550-556.

Wan, W., et al. (2014). Pyrrolysyl-tRNA synthetase: an ordinary enzyme but an outstanding genetic code expansion tool. Biochimica et Biophysica Acta (BBA)—Proteins and Proteomics, 1844(6), 1059-1070.

Wang, B., et al. (2003). The role and potential of sialic acid in human nutrition. European journal of clinical nutrition, 57(11), 1351-1369.

Wang, L., et al. (2003). Unnatural amino acid mutagenesis of green fluorescent protein. The Journal of organic chemistry, 68(1), 174-176.

Wissner, R. F., et al. (2013). Labeling proteins with fluorophore/ thioamide Forster resonant energy transfer pairs by combining unnatural amino acid mutagenesis and native chemical ligation. Journal of the American Chemical Society, 135(17), 6529-6540.

Wormald, M. R., et al. (2002). Conformational studies of oligosaccharides and glycopeptides: complementarity of NMR, X-ray crystallography, and molecular modelling. Chemical Reviews, 102(2), 371-386.

Xie, J., et al. (2007). A genetically encoded metabolically stable analogue of phosphotyrosine in *Escherichia coli*. ACS chemical biology, 2(7), 474-478.

Zabel, U., et al. (1993). Nuclear uptake control of NF-kappa B by MAD-3, an I kappa B protein present in the nucleus. The EMBO journal, 12(1), 201-211.

\* cited by examiner

O-GlcNAc-puromycin

ENGINEERED BACTERIAL RIBOSOME COMPOSITIONS AND METHODS

CROSS-REFERENCE TO RELATED APPLICATIONS

This application claims the benefit of U.S. Provisional Patent Application No. 62/811,638, filed Feb. 28, 2019, which is incorporated by reference herein as if set forth in its entirety.

STATEMENT REGARDING FEDERALLY SPONSORED RESEARCH

This invention was made with government support under R01 GM103861 awarded by the National Institutes of Health. The government has certain rights in the invention.

REFERENCE TO A SEQUENCE LISTING SUBMITTED VIA EFS-WEB

The content of the ASCII text file of the sequence listing named "112624_01171_ST25.txt" which is 0.562 kb in size was created on Jun. 13, 2020 and electronically submitted via EFS-Web herewith the application is incorporated herein by reference in its entirety.

FIELD OF THE DISCLOSURE

This disclosure is related to compositions and methods involving ribosomes engineered to incorporate glycosylated amino acids into proteins.

BACKGROUND

Proteins containing carbohydrates attached to key amino acid residues play important roles in numerous biological processes; essential functions include protein folding and stabilization. The initial observations of protein glycosylation were made for prokaryotic cell surface proteins, but it is now understood that protein glycosylation is a feature of all kingdoms of life. The most commonly glycosylated amino acid residues are asparagine (N-glycosylation); tyrosine, threonine and serine (O-glycosylation) and tryptophan (C-glycosylation). N-glycosylation involves covalent attachment via the amide nitrogen of Asn, and occurs co-translationally; it is the most common type of glycosylation (~90% of glycosylated proteins). O-glycosylation is a post-translational modification involving the OH groups of Ser, Tyr or Thr; it most commonly occurs in the Golgi apparatus and is initiated by the addition of a GalNAc residue to the β-OH group of Ser or Thr.

Although O-linked glycoproteins are somewhat less common, they are prominent in immunoglobulins, which are heavily O-glycosylated, and in the cytokines important in cell signaling. C-glycosylation represents a different type of carbohydrate attachment to proteins, mostly involving mannose, which is attached to Trp via C-2 of the indole ring. This modification occurs in the sequence WXXW (SEQ ID NO: 1), as demonstrated for properdin, a positive regulator of complement. It also occurs in human RNase 2 and interleukin-12. The biological function of C-glycosylation is not yet well understood.

Enzymes that transfer mono- or oligosaccharides from donor molecules to growing oligosaccharide chains on proteins are called glycosyltransferases (Gtfs). Each Gtf is specific for linking a particular sugar from a donor (sugar nucleotide or dolichol) to a substrate and acts independent of other Gtfs and glycosidases, the inevitable substrate specificity issues make post-translational sugar remodeling challenging to study. Molecular events involved in glycosylation include linking monosaccharides together, transferring sugars from one substrate to another and trimming sugars from the glycan structure. Unlike cell processes such as transcription or translation, glycosylation is not templated; thus, all of these steps do not necessarily occur during every glycosylation event.

As the foregoing description suggests, both the natural and artificial engineering of glycoproteins are rather complex. Accordingly, there remains a need to engineer modified ribosomes which incorporate glycosylated amino acids into proteins.

SUMMARY OF THE DISCLOSURE

In certain embodiments, compositions comprising a bacterial ribosome selected to increase the incorporation of a glycosylated amino acid into a protein versus a wild type bacterial ribosome are disclosed. In particular embodiments, a bacterial ribosome has been selected with a puromycin derivative, such as O-GlcNAc-puromycin.

Still further embodiments relate to methods for selecting a ribosomal clone configured to incorporate glycosylated amino acids into proteins. In some embodiments, methods include growing bacteria in the presence of a puromycin derivative and selecting sensitive clones. By way of example, a selected clone that includes a ribosome that incorporates at least one glycosylated amino acid into a protein is further validated.

Additional embodiments relate to methods for synthesizing a glycosylated protein with a selected bacterial ribosomal clone grown in the presence of a puromycin derivative.

These and other aspects will be apparent upon reference to the following detailed description and figures. To that end, any patent and other documents cited herein are hereby incorporated by reference in their entirety.

DETAILED DESCRIPTION OF THE DISCLOSURE

Figure 1:
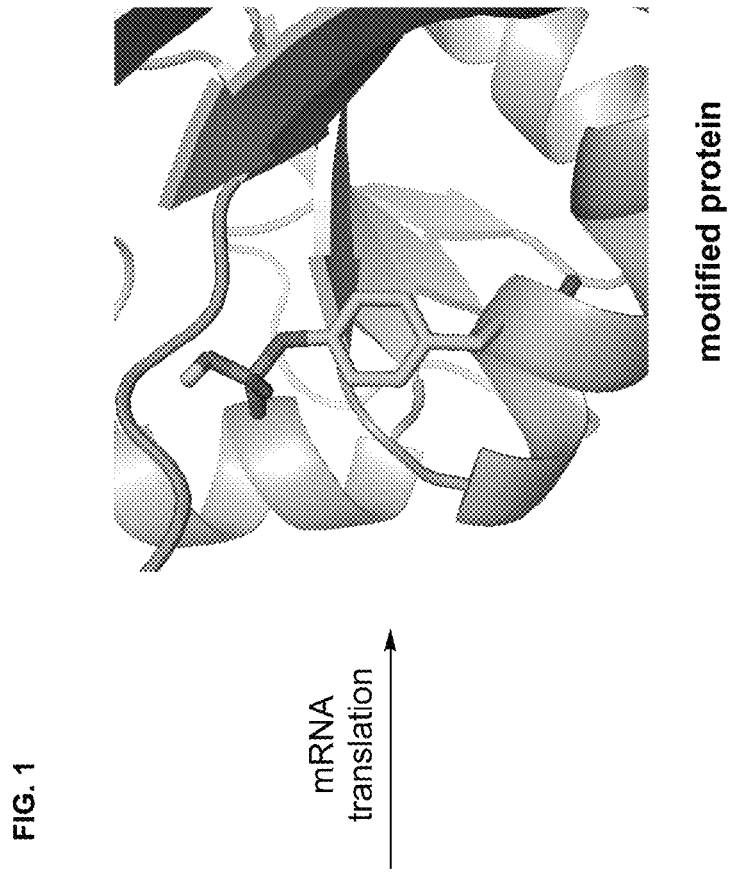
FIG. 1 schematically depicts the use of a suppressor tRNA activated with a glycosylated tyrosine to enable the incorporation into a protein of a modified amino acid usually modified post-translationally.
Figure 1:
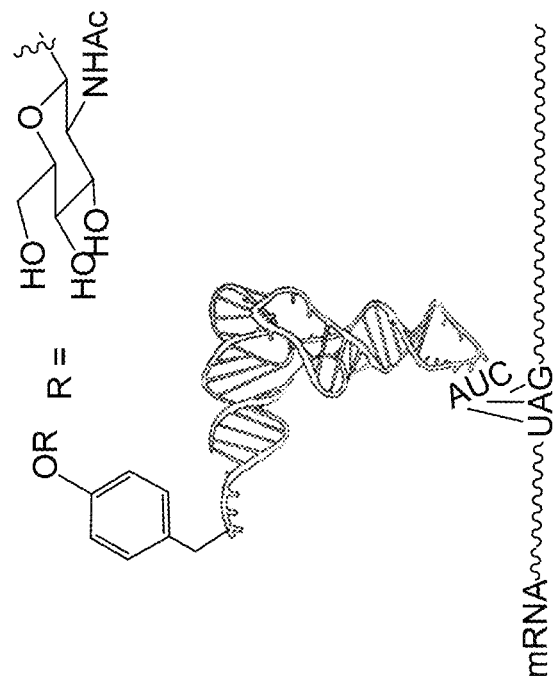

The technology disclosed herein is described in one or more exemplary embodiments in the following description with reference to the Figures (FIGS), in which like numbers represent the same or similar elements. Reference throughout this specification to "one embodiment," "an embodiment," or similar language means that a particular feature, structure, or characteristic described in connection with the embodiment is included in at least one embodiment of the present technology disclosed herein. Thus, appearances of the phrases "in one embodiment," "in an embodiment," and similar language throughout this specification may, but do not necessarily, all refer to the same embodiment.

The described features, structures, or characteristics of the technology disclosed herein may be combined in any suitable manner in one or more embodiments. In the following description, numerous specific details are recited to provide a thorough understanding of embodiments of the technology disclosed herein. One skilled in the relevant art will recognize, however, that the technology disclosed herein may be practiced without one or more of the specific details, or with other methods, components, materials, and so forth. In other instances, well-known structures, materials, or operations are not shown or described in detail to avoid obscuring aspects of the technology disclosed herein.

By reengineering the bacterial ribosome, the inventors have produced modified ribosomes which exhibit a 10-fold increase in the incorporation of N-acetylglucosaminyltyrosine into position 29 of interferon-β (INF-β), and which has also enabled preparation of IFN-β containing N-acetylglucosaminylserine at this position. Thus, it is believed that it will now be possible to prepare amounts of glycosylated proteins entirely sufficient for biochemical experiments. Most of the literature dealing with such post-translationally modified proteins has involved the study of protein structure and function at the whole cell level, often reaching conclusions based on structural inferences gathered from indirect observations. Access to quantities of homogeneous glycosylated proteins will enable putative pathways to be probed directly.

Embodiments herein disclose novel methods to create reengineered bacterial ribosomes specifically selected for their ability elaborate proteins incorporating unusual amino acid analogues not recognized by wild-type ribosomes. In some embodiments, such ribosomes are utilized to prepare proteins incorporating non-a-L-amino acids, and have carefully documented their presence and properties; these ribosomes also still incorporate the normal proteinogenic amino acids with acceptable fidelity. In further embodiments, preparation of ribosomes that can incorporate glycosylated amino acids into predetermined positions in proteins are contemplated. Such proteins have been very difficult to obtain in homogeneous form, which has limited the way in which biochemical processes involving glycosylation can be studied. In still other embodiments, the nature of the carbohydrate modification at position 29 of murine interferon-α is contemplated, as is the study of systematic modification on its antiviral activity. None of these experiments can readily be carried out using current technologies.

As used herein, the terms "peptide," "polypeptide," and "protein" are used interchangeably to refer to a polymer of amino acid residues. The terms apply to amino acid polymers in which one or more amino acid residues is an artificial chemical analog of a corresponding naturally occurring amino acid, as well as to naturally occurring amino acid polymers. The terms polypeptide, peptide, and protein are also inclusive of modifications including, but not limited to, glycosylation, lipid attachment, sulfation, carboxylation, hydroxylation, ADP-ribosylation, and addition of other complex polysaccharides. The terms "residue" or "amino acid residue" or "amino acid" are used interchangeably to refer to an amino acid that is incorporated into a peptide, protein, or polypeptide. The amino acid may be a naturally occurring amino acid and, unless otherwise limited, may encompass non-natural analogues of natural amino acids that can function in a similar manner as naturally occurring amino acids.

Non-Limiting Examples

Embodiments include the development of a generalizable technique for reengineering the bacterial ribosome via modification of key regions of 23S rRNA, including the identification of several regions of 23S rRNA amenable to alteration without substantial loss of the fidelity of protein synthesis, and use of these regions to produce optimized ribosomes. Furthermore, the development/implementation of a facile assay system for physicochemical characterization of amino acid incorporation by incorporating representative beta-amino acids into proteins efficiently and without undue loss of fidelity defining the position, shape, and stereochemistry of substituents in the beta-amino acids amenable to incorporation into proteins by the optimized ribosomes is contemplated.

The foregoing results suggest a rather direct approach for developing ribosomal clones capable of incorporating glycosylated amino acids into proteins, namely the use of appropriately constituted puromycin derivatives. As used herein, the term "puromycin derivative" refers to a modified or variant of the peptidyl nucleoside puromycin and encompasses puromycin variants comprising a glycosylated amino acid constituent such as glycosylated puromycins (e.g., O-GlcNAc-puromycin). Preferably, the puromycin variant comprises an amino acid constituent having a structure analogous to a given amino acid chosen to be incorporated into a protein. In some embodiments, a few selections with different puromycin derivatives is done. For each of these, we proceed as follows: prepare a puromycin derivative containing a glycosylated amino acid constituent closely related in structure to the glycosylated amino acid we wish to incorporate into proteins; screen our large library of clones harboring plasmids containing modified rrnB operons for sensitivity to the puromycin derivative being studied; typically 500-1,000 clones will be screened initially for promising clones; carry out secondary assays (generation time, dose dependency of sensitivity to the puromycin derivative, IC50 values for inhibition) to identify the most promising clones for more detailed investigation; determine nonspecific mRNA readthrough of clones in cellulo using a gene for β-galactosidase having a nonsense codon in position 17; challenge the prioritized clones with higher concentrations of erythromycin (to which the wild-type ribosomes are sensitive) to force them to use their modified ribosomes for survival and growth; prepare S-30 extracts from prioritized clones and attempt to incorporate the modified amino acid of interest from a misacylated suppressor tRNA transcript; verify that the in vitro protein synthesis with the modified ribosomes is sensitive to the puromycin derivative used for its selection; test successful S-30 extracts to see whether they can produce wild-type proteins having the same specific activity as proteins prepared using wild-type ribosomes. As used herein, the term "S-30 extract" refers to a cell-free protein synthesis system that involves E. coli extracts. Although S-30 extract preparations are demonstrated herein, it will be understood that other protein synthesis protocols including, without limitation, recombinant protein synthesis methods and automated peptide synthesis can be used to obtain glycosylated proteins, puromycin derivatives, and other polypeptides disclosed herein.

Figure 2:
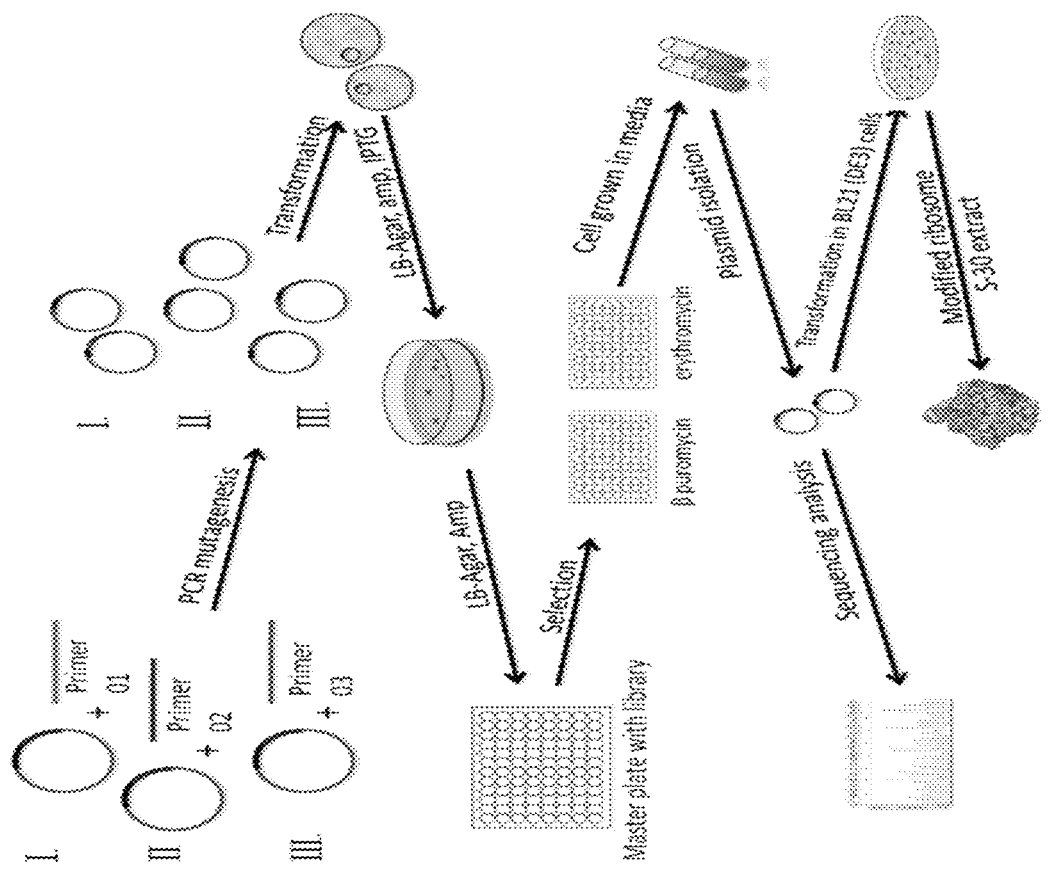
FIG. 2. Scheme employed for the selection of clones sensitive to the glycosylated puromycin shown. Members of an established E. coli library harboring plasmids with the rrnB operon modified in two regions of the DNA sequence for 23S ribosomal RNA known to be involved in forming the peptidyltransferase center of the ribosome were assayed for their sensitivity to each of the puromycins and their resistance to erythromycin. The most promising clones were analyzed using a number of secondary assays and quality control experiments; the final prioritized clones were used to prepare S-30 extracts which were employed in the experiments described herein.
Figure 2:
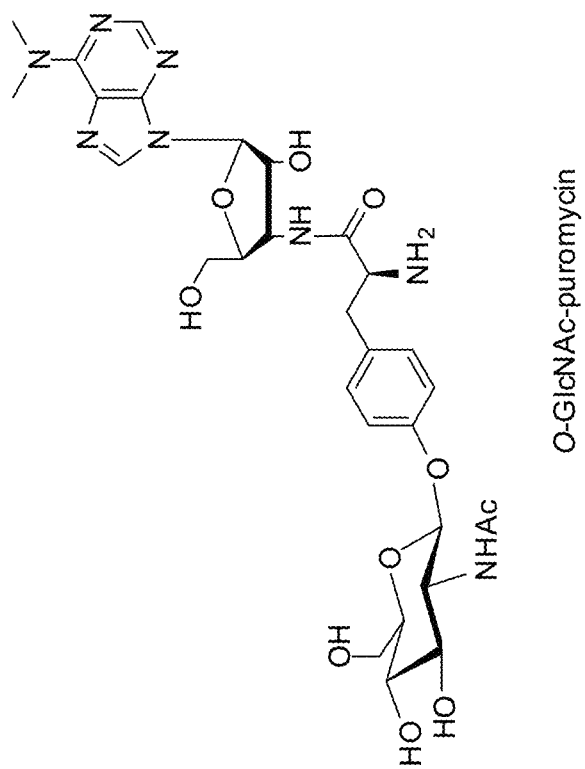

The key features of the selection process are outlined in FIG. 2. The mutagenesis for library creation was done in a background of moderate erythromycin resistance; since erythromycin binds close to the peptidyltransferase center, this enabled identification/elimination of mutants having undergone large structural changes in the peptidyltransferase center.

Figure 3:
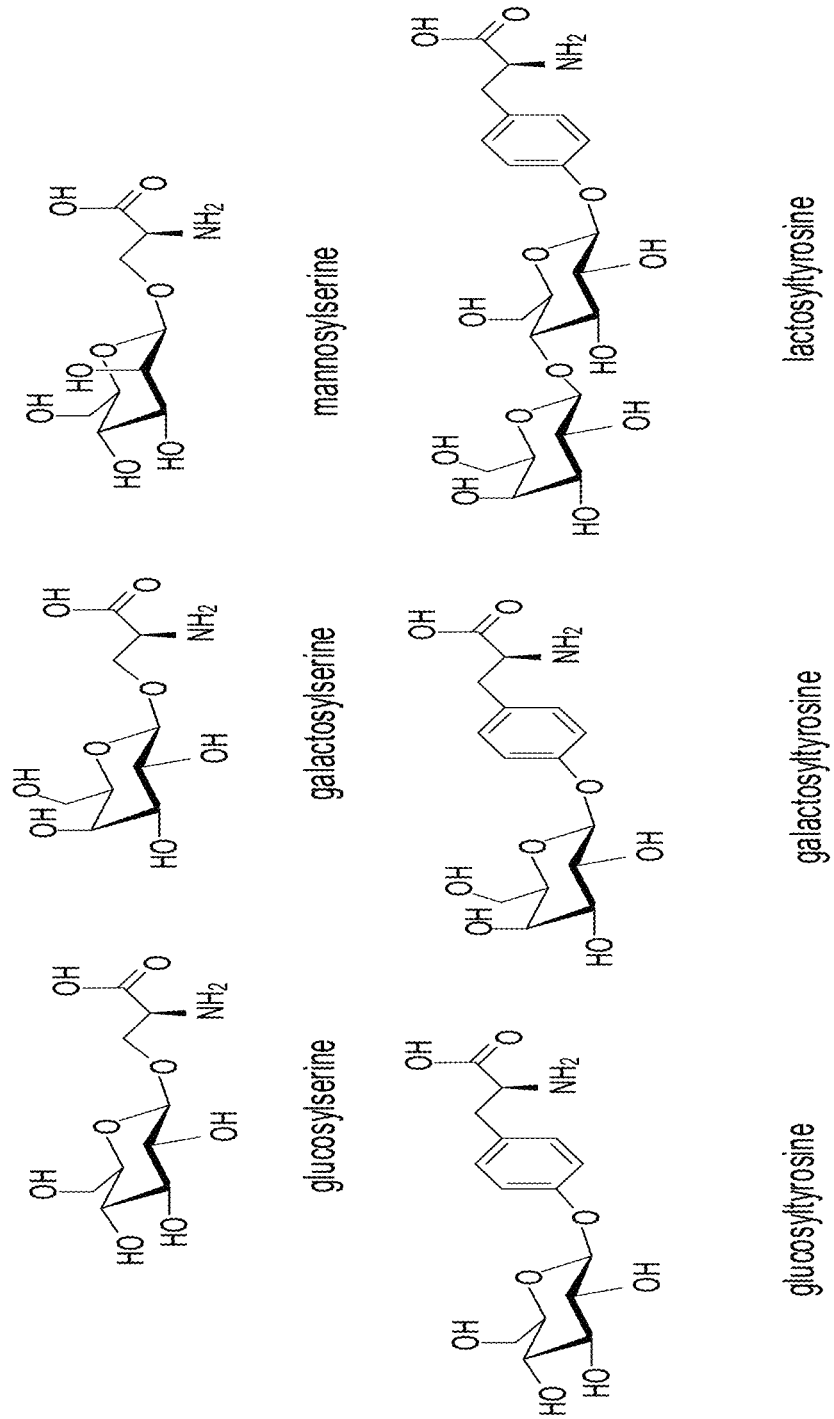
FIG. 3 depicts glycosylated amino acids incorporated into proteins by wild-type E. coli ribosomes.
Figure 4:
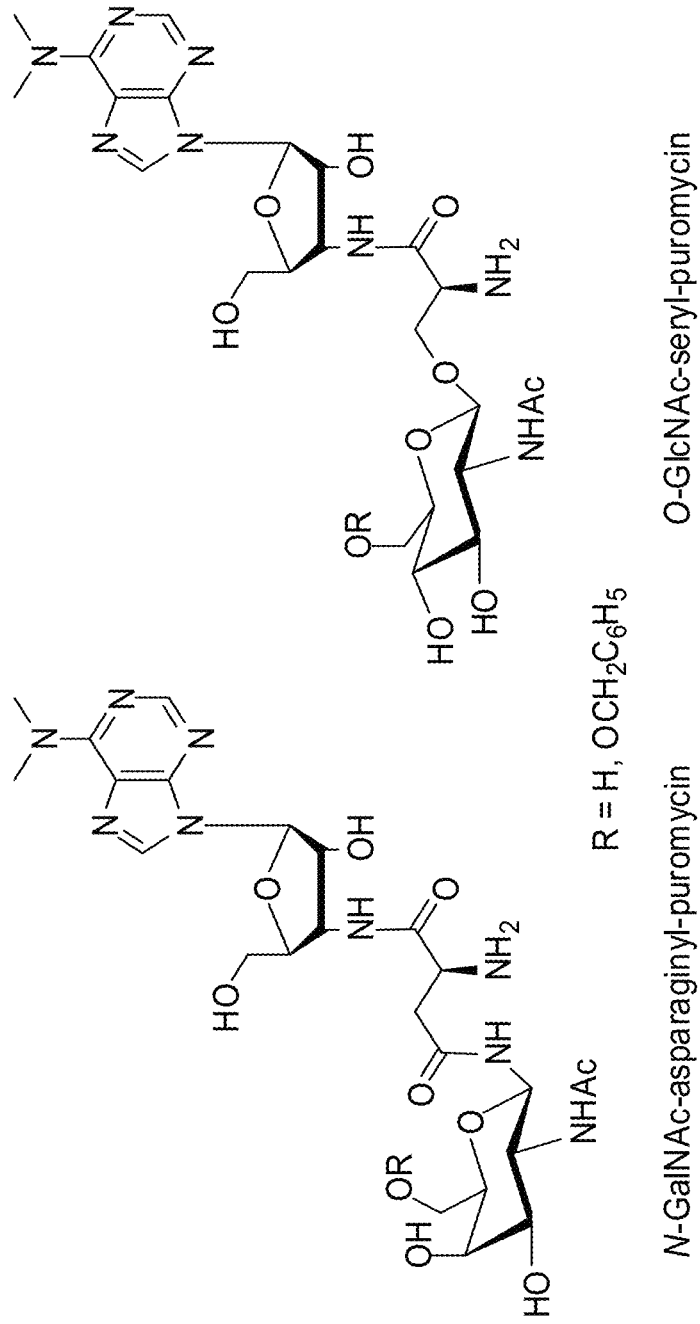
FIG. 4. Glycosylated puromycins proposed for synthesis and evaluation.

Many glycosylated amino acids can be incorporated into proteins in quite good yield from activated suppressor tRNAs by nonsense codon suppression employing wild-type ribosomes. Several examples are shown in FIG. 3. However, in numerous experiments, when any of these was O- or N-acetylated at one or more positions, the result was virtually complete loss of the ability of the activated tRNAs to suppress nonsense codons. Accordingly, we have used O-GlcNAc-puromycin (FIG. 4) to select modified ribosomes capable of incorporating N-acetylglycosyl amino acids.

The initial screening for ribosomal clones inhibited by O-GlcNAc-puromycin involved 793 clones. As shown in Table 1, five variants (clones) were deemed to be useful for preparing N-acetylated glycosylated proteins, and are thought to be useful for preparing IFN-β having two different N-acetylglycosyl amino acids in position 29.

Further embodiments involve the selection of ribosomes that facilitate the introduction of carbohydrates into predetermined sites in proteins, particularly N-acetylated sugars such as GlcNAc and GalNAc. Specific embodiments include introduction of glycosylated amino acids into position 29 of murine interferon β. Asn29 is known to be N-glycosylated in the native protein via a GlcNAc residue. Sugar removal/modification has been reported to have unusual effects on antiviral activity of the protein.

As used herein, the term "glycosylation" refers to a co-translational or post-translational process modifications by which a sugar pendent group or "glycan" is added to a substrate such as proteins, lipids, or other organic molecules. The term encompasses N-linked glycosylation, in which a sugar group is added to an asparagine side chain, and O-linked glycosylation, in which a sugar group is added to a serine or threonine amino acid side chain. Glycosylation is an enzyme-mediated process.

Post-translational protein glycosylation is both ubiquitous in nature and quite important. We have previously demonstrated that unmodified ribosomes can incorporate a variety of glycosylated amino acids into proteins in good suppression yields. However, for whatever reason(s), neither O- nor N-acetylated glycosyl amino acids could be incorporated in good yield with wild-type ribosomes. We wish to select modified ribosomes capable of incorporating O- or N-acetylated glycosyl amino acids efficiently.

Incorporation of O-(N-acetylglucosyl)tyrosine into position 29 of interferon β (IFN-β). Using O-GlcNAc-puromycin, (FIG. 2), it was shown that selecting ribosomes sensitive to this puromycin analogue (Table 1) was achieved. As shown in Table 2, four of these variants (clones) were found to incorporate O-(N-acetylglucosaminyl)tyrosine into position 29 of interferon β (IFN-β) in yields ranging from 9-17%. These yields are sufficient to support our proposed experiments with IFN-β but it would be of significant advantage to be able to have modified ribosomes that produced glycosylated proteins more efficiently. This may be achieved by increasing the number of clones screened. In our initial experiments, 793 ribosomal clones were tested.

TABLE 1

Characterization of variants of rrnB operon selected with GlcNAc-puromycin.

| name of variant | selection data (% inhibition) | sequence in the mutagenized regions | |
|---|---|---|---|
| | | region 1 | region 2 |
| 010211 | 51.8 (36.1)[a] | $^{2057}$UGCGUGG$^{2063}$ | $^{2496}$GGGAAG$^{2501}$ |
| 010252 | 45.8 (40.1)[a] | $^{2057}$UGCGUGG$^{2063}$ | $^{2496}$TCGAGA$^{2501}$ |
| 010309 | 87.5 (56.5)[a] | $^{2057}$UGCGUGG$^{2063}$ | $^{2502}$CTACGG$^{2507}$ |
| 010312 | 61.4 (52.2)[a] | $^{2057}$UGCGUGG$^{2063}$ | $^{2502}$CTCCAG$^{2507}$ |
| 010328 | 41.5 (57.3)[a] | $^{2057}$UGCGUGG$^{2063}$ | $^{2502}$CTACAG$^{2507}$ |
| wt | <10% | $^{2057}$GAAAGAC$^{2063}$ | $^{2496}$CACCTC$^{2501}$ $^{2502}$GATGTC$^{2507}$ |

[a]Data from repeated selection experiment.

TABLE 2

Synthesis of IFN-β from modified gene (TAG codon in position 29) in the presence of GlcNAc-tyrosyl-tRNA$_{CUA}$ using different S-30 preparations

| S-30 | sequence of the second mutagenized region of modified ribosomes | translation yield[a] in the presence of GlcNAc-tyrosyl-tRNA$_{CUA}$ (%) |
|---|---|---|
| wild-type | $^{2496}$CACCUC$^{2501}$ $^{2502}$GAUGUC$^{2507}$ | 1.5 |
| 010211 | $^{2496}$GGGAAG$^{2501}$ | 16 (17)[b] |
| 010252 | $^{2496}$UCGAGA$^{2501}$ | 14 |
| 010312 | $^{2502}$CUCCAg$^{2507}$ | 9 |
| 010328 | $^{2502}$CUACAg$^{2507}$ | 11 (9)[b] |

[a]Percentage relative to protein synthesis from wild-type gene; [b]repeated experiment While the suppression yields realized with GlcNAc-tyrosyl-tRNA$_{CUA}$ were acceptable, it may be possible that these modified ribosomes will not be useful for UAG codon suppression with GlcNAc-seryl-tRNA$_{CUA}$. We have shown that GlcNAc-seryl-tRNA$_{CUA}$ is incorporated very poorly by wild-type ribosomes. Since GlcNAc (protein-linked through Asn residues) and GalNAc (linked via Ser or Thr) are very important constituents of glycoproteins, it is anticipated that ribosomes may be selected for their incorporation. If difficulty is encountered in identifying suitable clones using the puromycins in FIG. 4, attachment of an aromatic substituent to one of the sugar O-atoms in the puromycins may be needed (as exemplified in FIG. 4). This strategy was used for the selection of ribosomes capable of incorporating beta-amino acids, and found that they also worked well on unsubstituted beta-amino acids.

Functional evaluation of IFN-β analogues. Murine interferon-β has been characterized in detail in regard to the location and nature of its attached carbohydrates. Asparagine residues at positions 29, 69 and 76 are N-glycosylated. The sugar N-linked to Asn is GlcNAc, and each site contains 9-11 attached sugars. In a study of the antiviral activity of murine INF-β, it was found that site directed mutagenesis (replacing Asn with Asp at the three glycosylation sites, and thereby precluding glycosylation at those sites), greatly reduced antiviral activity, but had a lesser effect when at least one of sites was glycosylated. Glycosylation of Asn29 alone afforded IFN-β having antiviral activity reduced only two-fold from wild-type. It was also noted that the attached carbohydrates had little effect on receptor binding per se, but that while the replacement of Asn29 with Asp29 reduced wild-type antiviral activity only two-fold, replacement of Asn29 with Ala29 reduced antiviral activity 10-fold.

Figure 5:
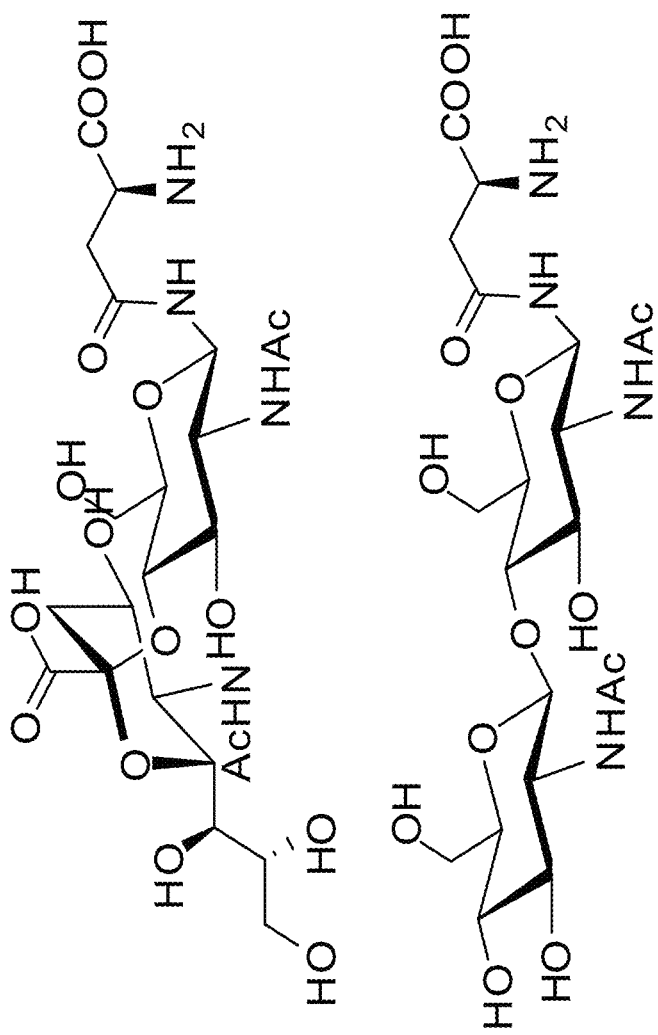
FIG. 5 shows NeuAcα2→4GlcNAc-Asn (top) and GlcNAc1→4GlcNAc-Asn (bottom).

In further embodiments, we prepared the two disaccharides shown in FIG. 5, one containing a sialic acid residue linked to GlcNAc-Asn, and the other containing GlcNAc-GlcNAc-Asn (as is actually found for the first two sugar residues in IFN-β). Both of these disaccharides were introduced into position 29 of IFN-β during in vitro protein synthesis using appropriate modified ribosomes. (As noted in FIG. 3, O-lactosyltyrosine was actually incorporated into proteins quite well even by wild-type ribosomes). Control INF-βs were also prepared containing Ala and Asp at position 29.

Figure 6:
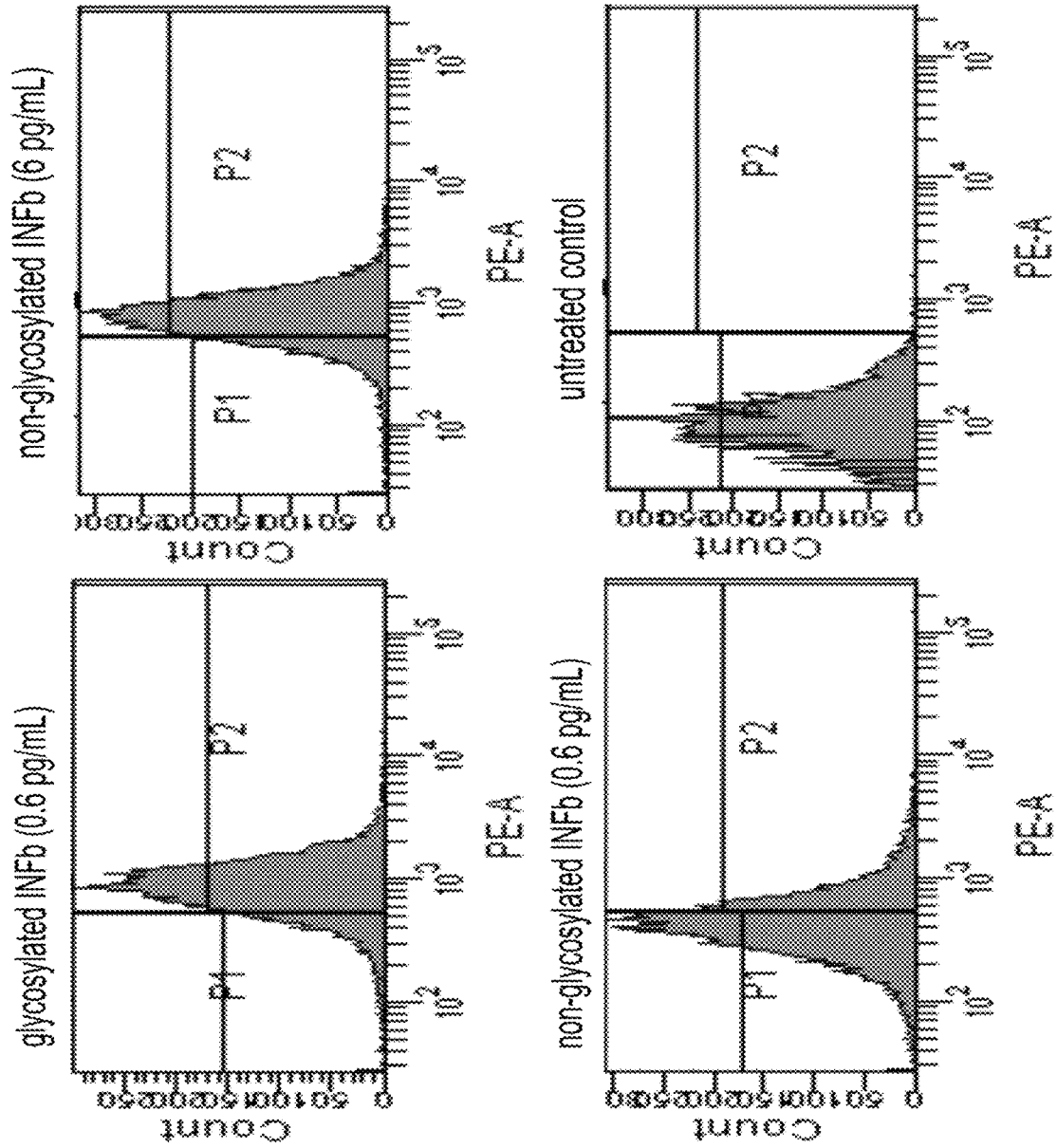
FIG. 6. Flow cytometry analysis of RAW 264.7 cells treated with murine IFNs and probed with PE-conjugated anti-mouse CD40 antibody. Upper left, 0.6 pg/mL glycosylated IFN; upper right, 6 pg/mL non-glycosylated IFN; lower left, 0.6 pg/mL non-glycosylated IFN; lower right, control lacking IFN.

These four modified INF-βs were tested in parallel with wild-type (fully glycosylated) mouse IFN-β for their activities. Our assay system uses RAW 264.7 mouse macrophage cells (ATCC TIB-71), which have been transformed using Abelson murine leukemia virus. IFN-β upregulates CD40 expression in these cells, which is displayed on the cell surface. CD40 upregulation was probed using a PE (phycoerythrin)-conjugated anti-mouse CD40 antibody. As shown (FIG. 6), this assay system has been used successfully to compare fully glycosylated and non-glycosylated murine INF-βs by flow cytometry. Both gave dose-dependent responses; consistent with the reported difference in antiviral potencies for the glycosylated and non-glycosylated INF-βs, we found that glycosylated IFN-β was about 10-fold more potent than non-glycosylated IFN-β.

The ability to produce specifically glycosylated proteins would be of greatest utility if it could be realized in intact cells.

In cellulo incorporation of modified amino acids. The development of orthogonal pair technology has enabled the incorporation of more than 100 unnatural amino acids into different proteins in cellulo. While amino acids not recognized by wild-type ribosomes can presently not be incorporated into proteins within cells, our efforts over the last decade to create modified ribosomes capable of incorporating non-alpha-amino acids into proteins offers a potential solution to this problem.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

The terms "comprising", "comprises" and "comprised of" as used herein are synonymous with "including", "includes" or "containing", "contains", and are inclusive or open-ended and do not exclude additional, non-recited members, elements, or method steps. The phraseology and terminology used herein is for the purpose of description and should not be regarded as limiting. The use of "including," "comprising," "having," "containing," "involving," and variations thereof, is meant to encompass the items listed thereafter and additional items. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of" "Consisting essentially of" when used in the claims, shall have its ordinary meaning as used in the field of patent law.

As used herein, the terms "approximately" or "about" in reference to a number are generally taken to include numbers that fall within a range of 5% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

It should also be understood that, unless clearly indicated to the contrary, in any methods claimed herein that include more than one step or act, the order of the steps or acts of the method is not necessarily limited to the order in which the steps or acts of the method are recited.

The claims are not meant to be limited to the materials and methods, embodiments, and examples described herein.

We claim:

1. An *Escherichia coli* (*E. coli*) bacterial ribosome comprising a modified 23S ribosomal RNA sequence comprising modifications as compared to a wild-type counterpart, wherein the modifications consist of a first modified region and a second modified region;
   wherein the 23S ribosomal RNA is expressed from an engineered rrnB operon;
   wherein the first modified region consists of the sequence UGCGUGG from position 2057 to 2063;
   wherein the second modified region consists of a sequence selected from GGGAAG and UCGAGA from position 2496 to 2501;
   wherein a DNA sequence encoding a first unmodified region of the wild-type counterpart consists of the sequence GAAAGAC from position 2057 to 2063; and
   wherein a second unmodified region of the wild-type counterpart consists of the sequence CACCUC from position 2496 to 2501.

2. The *E. coli* bacterial ribosome of claim 1, wherein the second modified region consists of GGGAAG from position 2496 to 2501.

3. The *E. coli* bacterial ribosome of claim 1, wherein the second modified region consists of UCGAGA from position 2496 to 2501.

4. A composition comprising the modified *E. coli* bacterial ribosome of claim 1.

5. The composition of claim 4, comprising a bacterial extract.

6. The composition of claim 4, comprising a cell-free translation system.

7. The composition of claim 4, comprising a cell-free bacterial translation system.

8. The composition of claim 7, comprising an *E. coli* bacterial extract.

9. The composition of claim 8, comprising a bacterial cell-free translation system.

10. The composition of claim 9, comprising an *E. coli* cell-free translation system.

11. A cell comprising the modified bacterial ribosome of claim 1.

* * * * *

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(3)
<223> OTHER INFORMATION: Xaa can be any naturally occurring amino acid

<400> SEQUENCE: 1

Trp Xaa Xaa Trp
1
```